(12) United States Patent
Zahalka et al.

(10) Patent No.: US 8,258,214 B2
(45) Date of Patent: Sep. 4, 2012

(54) POLYMERS WITH LOW GEL CONTENT AND ENHANCED GAS-FADING

(75) Inventors: Hayder Zahalka, Morgantown, WV (US); Michael E. Gelbin, Middlebury, CT (US); Maurice Power, Manchester (GB); Jonathan S. Hill, Manchester (GB)

(73) Assignee: Chemtura Corporation, Middlebury, CT (US)

( * ) Notice: Subject to any disclaimer, the term of this patent is extended or adjusted under 35 U.S.C. 154(b) by 0 days.

(21) Appl. No.: 13/272,298

(22) Filed: Oct. 13, 2011

(65) Prior Publication Data

US 2012/0035305 A1 Feb. 9, 2012

Related U.S. Application Data

(60) Division of application No. 12/604,981, filed on Oct. 23, 2009, now Pat. No. 8,188,170, which is a continuation-in-part of application No. 11/787,531, filed on Apr. 16, 2007, now Pat. No. 7,888,414.

(60) Provisional application No. 60/815,819, filed on Jun. 20, 2006.

(51) Int. Cl.
*C08K 5/34* (2006.01)

(52) U.S. Cl. .................. 524/101; 524/128; 524/384

(58) Field of Classification Search .................. 524/101, 524/128, 384
See application file for complete search history.

(56) References Cited

U.S. PATENT DOCUMENTS

| | | | |
|---|---|---|---|
| 2,220,845 A | 11/1940 | Moyle | |
| 2,834,798 A | 5/1958 | Hechenbleikner et al. | |
| 3,412,064 A | 11/1968 | Brindell | |
| 3,492,377 A | 1/1970 | Kline | |
| 3,558,554 A | 1/1971 | Kuriyama et al. | |
| 3,644,536 A | 2/1972 | Bafford | |
| 3,755,200 A | 8/1973 | Rhodes et al. | |
| 3,756,906 A | 9/1973 | Nicholas et al. | |
| 3,787,537 A | 1/1974 | De Marcq | |
| 4,261,880 A | 4/1981 | Fujii et al. | |
| 4,276,233 A | 6/1981 | Markezich et al. | |
| 4,321,218 A | 3/1982 | Rasberger | |
| 4,383,950 A | 5/1983 | Rasberger | |
| 4,406,842 A | 9/1983 | Spivack | |
| 4,492,661 A | 1/1985 | Maul et al. | |
| 4,540,538 A | 9/1985 | Corwin et al. | |
| 4,719,257 A | 1/1988 | Ishii et al. | |
| 4,829,112 A | 5/1989 | Ishii et al. | |
| 5,208,368 A | 5/1993 | Scherzer et al. | |
| 5,254,610 A | 10/1993 | Small, Jr. et al. | |
| 5,254,709 A | 10/1993 | Hunter | |
| 5,322,871 A | 6/1994 | Pitteloud et al. | |
| 5,401,845 A | 3/1995 | Pitteloud et al. | |
| 5,561,181 A | 10/1996 | Mahood | |
| 6,576,788 B1 | 6/2003 | Penzel et al. | |
| 6,824,711 B2 | 11/2004 | Stevenson et al. | |
| 6,846,859 B2 | 1/2005 | Coffy et al. | |
| 6,887,926 B1 | 5/2005 | Parhar et al. | |
| 7,157,511 B2 | 1/2007 | Bobsein et al. | |
| 7,320,764 B2 | 1/2008 | Stevenson et al. | |
| 7,361,703 B2 | 4/2008 | Tikuisis et al. | |
| 7,468,410 B2 | 12/2008 | Chafin et al. | |
| 2003/0078340 A1 | 4/2003 | Fatnes et al. | |
| 2004/0048958 A1 | 3/2004 | Didier | |
| 2007/0149660 A1 | 6/2007 | Kumar et al. | |
| 2007/0228343 A1 | 10/2007 | Roth et al. | |

FOREIGN PATENT DOCUMENTS

| | | |
|---|---|---|
| CZ | 280 072 | 10/1995 |
| DE | 2940620 | 4/1981 |
| EP | 0 090 524 | 10/1983 |
| EP | 0 245 852 | 11/1987 |
| EP | 0 454378 A1 | 10/1991 |
| EP | 0551 062 | 7/1993 |
| GB | 1 298 248 | 11/1972 |
| GB | 2 227 490 | 8/1990 |
| GB | 2252324 A | 8/1992 |
| JP | 59 30842 | 2/1984 |
| JP | 5 202236 | 8/1993 |
| JP | 7 309884 | 11/1995 |
| RO | 112871 | 1/1998 |
| RU | 2 140 938 | 11/1999 |
| WO | WO 2007/009916 A1 | 1/2007 |
| WO | 2007/149143 | 12/2007 |

OTHER PUBLICATIONS

International Search Report mailed Dec. 6, 2007; of PCT Application No. PCT/US2007/009690: 3 pgs.
International Preliminary Report on Patentability mailed Dec. 22, 2008; of PCT Application No. PCT/US2007/009690: 6 pgs.

*Primary Examiner* — Peter D Mulcahy
(74) *Attorney, Agent, or Firm* — Joseph Suhadolnik

(57) ABSTRACT

A polymer stabilizing composition comprising a sterically hindered phenol and a phosphite that provides low gel content and enhanced resistance to gas-fading. The stabilizer composition is particular useful for stabilizing polyethylene homopolymers and copolymers, such as linear low density polyethylenes produced from metallocene catalyst. The sterically hindered phenol is, for example, selected from the group consisting of 1,3,5-tris-(4-tert-butyl-3-hydroxy-2,6-dimethylbenzyl)isocyanurate, 1,3,5-tris-(3,5-dicyclohexyl-4-hydroxybenzyl)isocyanurate, 1,3,5-tris-(3,5-di-tert-butyl-4-hydroxybenzyl)isocyanurate, 1,3,5-tris(4-t-butyl-3-hydroxy-2,6-dimethylbenzyl)-1,3,5-Triazine-2,4,6-(1H,3H,5H)-trione, and 1,3,5-tris-(3,5-di-tert-butyl-4-hydroxybenzyl)-2,4,6-trimethylbenzene.

20 Claims, No Drawings

POLYMERS WITH LOW GEL CONTENT AND ENHANCED GAS-FADING

This patent application is a divisional of U.S. patent application Ser. No. 12/604,981 filed Oct. 23, 2009, now U.S. Pat. No. 8,188,170, which is a continuation-in-part of U.S. patent application Ser. No. 11/787,531, filed Apr. 16, 2007, now U.S. Pat. No. 7,888,414, which claims priority to U.S. Provisional Application No. 60/815,819, filed Jun. 20, 2006.

FIELD OF INVENTION

The present invention relates to novel compositions of stabilizers for polymers that demonstrate low gel content and enhanced gas-fading. More specifically, the stabilizers comprise a sterically hindered phenol and a phosphite for stabilizing polyolefins.

BACKGROUND OF THE INVENTION

Polymers, e.g., polyolefins, polyvinyl halides, polyesters, polyamides, nitrile polymers, styrenic polymers and acrylate polymers, and elastomeric materials such as butadiene rubber, polyisoprene etc., are inherently unstable and susceptible to thermal oxidative degradation. Thus, these polymers and elastomeric material often require stabilization during melt processing. Exemplary stabilizers include phenolic antioxidants, hindered amine light stabilizers, ultraviolet light absorbers, organophosphites, antioxidants, metal salts of fatty acids, hydrotalcites, metal oxides, epoxidized oils, hydroxylamines, amine oxides, lactones, and thiosynergists.

Organophosphites are used broadly in the stabilization of polyolefins as non-discoloring antioxidants during melt processing, fabrication, and long term applications. Stabilization strategy of various polyethylene resins depends on the type (HDPE, LDPE, LLDPE, etc.), manufacturing process (gas-phase, slurry, solution), and catalyst (Ziegler-Natta. Chromium, metallocene, etc.) employed in the polymer production. Often times, the molar ratio of phosphite to hindered phenolics and the neutralizer package is dependent on the polymer grade. It is a common commercial practice to use combinations of sterically hindered phenols and phosphites in various molar ratios as a stabilizer system for polyethylene. Commonly used sterically hindered phenols include tetrakismethylene (3,5-di-t-butyl-4-hydroxyhydrocinnamate) methane, octyl-3-(3,5-di-t-butyl-4-hydroxyphenyl)propionate, bis(octadecyl)hydroxylamine, 3,5-bis(1,1-dimethylethyl)-4-hydroxy-benzenepropanoic acid and 2,6-di-t-butyl-4-ethyl-phenol. Commonly used phosphites include tris-nonylphenyl phosphite (TNPP) and tris(2,4-di-t-butylphenyl)phosphite, commercially sold under the trade names Alkanox™, 240 (Chemtura Corporation, Middlebury, Conn., USA), Irgafos™ 168 (Ciba Specialty Chemicals Corporation, Tarrytown, N.Y., USA), or Doverphos™ S-480 (Dover Chemical Corp, Dover, Ohio, USA).

TNPP and tris(2,4-di-t-butylphenyl)phosphite are commonly used in conjunction with octyl-3-(3,5-di-t-butyl-4-hydroxyphenyl)propionate for melt stabilization of polyethylene. However, combinations of phosphites with octyl-3-(3,5-di-t-butyl-4-hydroxyphenyl)propionate exhibit poor gas fading and high gel content when incorporated in polyethylene resins. Poor gas fading and high gel content render these stabilizers unsuitable for film applications. Without being bound to theory, it is believed that gels are small regions of high molecular weight polymers or loosely crosslinked polymers formed in the reactor and/or extruder, and are difficult to remove once formed. The gels are a common problem for low density polyethylenes and polyvinyl chlorides, and may cause distortions in film applications. Some prior attempts have been made to reduce gel content by adding anti-gel agents, such as polyethylene glycols/oxides or ethoxylated linear alcohols, as described in U.S. Pat. No. 4,540,538.

Thus, the need exists for safe and effective stabilizers that can effectively stabilize polymer resins and compositions against degradation.

SUMMARY OF THE INVENTION

The present invention, in one embodiment, is directed to a stabilizing composition for polyolefins comprising: (1) a sterically hindered phenol; and (2) a phosphite composition comprising at least two different phosphites of the following: (i) a tris(dialkylaryl)phosphite, (ii) a tris(monoalkylaryl)phosphite, (iii) a bis(dialkylaryl)monoalkylaryl phosphite, and (iv) a bis(monoalkylaryl)dialkylaryl phosphite; wherein the phosphite composition is a liquid at ambient conditions.

The sterically hindered phenol may be selected from the group consisting of 1,3,5-tris-(4-tert-butyl-3-hydroxy-2,6-dimethylbenzyl)isocyanurate, 1,3,5-tris-(3,5-dicyclohexyl-4-hydroxybenzyl)isocyanurate, 1,3,5-tris-(3,5-di-tert-butyl-4-hydroxybenzyl)isocyanurate, 1,3,5-tris(4-t-butyl-3-hydroxy-2,6-dimethylbenzyl)-1,3,5-Triazine-2,4,6-(1H,3H,5H)-trione, and 1,3,5-tris-(3,5-di-tert-butyl-4-hydroxybenzyl)-2,4,6-trimethylbenzene.

The phosphite composition may comprise from 0.1 to 20 wt. % of the tris(dialkylaryl)phosphite, based on the total weight of the phosphite composition; from 20 to 70 wt. % of the tris(monoalkylaryl)phosphite; from 2 to 20 wt. % of the bis(dialkylaryl)monoalkylaryl phosphite, and from 15 to 60 wt. % of the bis(monoalkylaryl)dialkylaryl phosphite.

In another embodiment, there is provided an article comprising: a) a polyolefin selected from the group consisting of polyethylene homopolymers, polyethylene copolymers, polypropylene homopolymers, and polypropylene copolymers; and b) an effective amount of a stabilizing composition. The stabilizing composition comprises (1) a sterically hindered phenol; and (2) a phosphite composition comprising at least two different phosphites of the following: (i) a tris(dialkylaryl)phosphite, (ii) a tris(monoalkylaryl)phosphite, (iii) a bis(dialkylaryl)monoalkylaryl phosphite, and (iv) a bis(monoalkylaryl)dialkylaryl phosphite; wherein the phosphite composition is a liquid at ambient conditions. Preferably, the polyolefin is linear low density polyethylene produced from a metallocene catalyst.

In such embodiments, the article may have a gel content, the size of the gel being 200 μm to 400 μm, of from 0.01 to 0.5 gel per square meter (gel/m$^2$) of film. Preferably, the composition has no detectable gel sized formations that are greater than 400 μm. Preferably, the composition is substantially free of anti-gel agents. In addition, the article may have a yellowness index after exposure to $NO_x$ for 7 days of less than 0, for 18 days of less than 0.7, for 25 days of less than 1.1, for 33 days of less than 1.7 or for 41 days of less than 2.5.

In one embodiment, is the article comprises from 250 to 5000 wppm of the stabilizing composition, based on the total weight of the article. The weight ratio of the sterically hindered phenol to the phosphite composition may be from 1:1 to 1:20 and in one embodiment from 1:10 to 1:20.

In yet another embodiment, there is provided an article comprising: (a) a polyolefin selected from the group consisting of polyethylene homopolymers, polyethylene copolymers, polypropylene homopolymers, and polypropylene copolymers; and (h) an effective amount of a stabilizing composition. The stabilizing composition comprises (1) a sterically hindered phenol; and (2) a phosphite selected from the group consisting of triphenyl phosphites, diphenylalkyl phosphites, phenyldialkyl phosphites, tris(nonyl-phenyl)phosphites, trilauryl phosphites, trioctadecyl phosphites, distearyl pentaerythritol diphosphites, tris(2,4-di-tert-butylphenyl) phosphites, diisodecyl pentaerythritol diphosphites, bis(2,4-di-tert-butylphenyl)pentaerythritol diphosphites tristearyl sorbitol triphosphites, bis(2,4-dicumylphenyl)pentaerythritol diphosphites, tetrakis(2,4-di-tert-butylphenyl)-4,4'-biphenylene diphosphonites or mixtures thereof. In this aspect, the article has a gel content, the gel being size 200 to 400 μm, of from 0.01 to 0.5 gel per square meter (gel/m$^2$) of the article.

DETAILED DESCRIPTION OF THE INVENTION

Introduction

The present invention relates to the stabilization of polymers using an effective amount of a stabilizing composition comprising a sterically hindered phenol and a phosphite, preferably a liquid phosphite. The stabilizer composition is particular useful for stabilizing polyolefins, such as polyethylenes and polypropylenes. The effective amount of a sterically hindered phenol and a phosphite of the invention contributes to increase color stability of the polyolefin when exposed to NO$_x$. Surprisingly and unexpectedly, the effective amount of the sterically hindered phenol and the phosphite further reduces gel content of the polyolefins. These improved properties lead to improved performance in the articles produced from the polyolefins.

A. Polymers

The polymers stabilized by the stabilizing compositions of the invention may be a polyethylene homopolymer or copolymer, or a polypropylene homopolymer or copolymer. Although the present invention is discussed in terms of polyethylene and polypropylene, other polymers known in the art, such as polyolefin homopolymers and copolymers, thermoplastics, rubbers, polyesters, polyurethanes, polyalkylene terephthalates, polysulfones, polyimides, polyphenylene ethers, styrenic polymers and copolymers, polycarbonates, acrylic polymers, polyamides, polyacetals, halide-containing polymers, and biodegradable polymers are contemplated by embodiments of the present invention.

In one embodiment, the polymers, typically ethylene based polymers, have a density in the range of from 0.86 g/cc to 0.97 g/cc, preferably in the range of from 0.88 g/cc to 0.965 g/cc, more preferably in the range of from 0.900 g/cc to 0.96 g/cc, even more preferably in the range of from 0.905 g/cc to 0.95 g/cc, yet even more preferably in the range from 0.910 g/cc to 0.940 g/cc, and most preferably greater than 0.915 g/cc. The polymers of the invention may have a narrow, wide or bimodal molecular weight distribution, a weight average molecular weight to number average molecular weight (Mw/Mn) of from about 1.5 to about 15, particularly from about 2 to about 10, more preferably from about 2.2 to about 8, even more preferably from about 2.2 to about 5, and most preferably from about 2.5 to about 4. In one embodiment, the polymers of the present invention may have a tailored molecular weight distribution. The ratio of Mw/Mn can be measured by gel permeation chromatography techniques well known in the art. The polymers of the present invention, in one embodiment, have a melt index (MI) or (I2), as measured by ASTM-D-1238-E, in the range from 0.01 to 1000 g per 10 mins, more preferably from about 0.01 to about 100 g per 10 mins, even more preferably from about 0.1 to about 50 g per 10 mins, and most preferably from about 0.1 to about 10 g per 10 mins. The polymers of the invention, in one embodiment, have a melt index ratio (I21/I2) (I21 is measured by ASTM-D-1238-F) of from 10 to 25, e.g., from 15 to 5. The polymers of the invention, in a preferred embodiment, have a melt index ratio (I21/I2) (I21 is measured by ASTM-D-1238-F) of from preferably greater than 25, more preferably greater than 30, even more preferably greater that 40, still even more preferably greater than 50 and most preferably greater than 65.

Non-limiting polymers include ethylene based polymers such as linear low density polyethylene (LLDPE), low density polyethylene (LDPE), copolymers of ethylene and olefins having 3 or more carbon atoms, e.g., 3-12 carbon atoms, and propylene based polymers such as polypropylene polymers including atactic, isotactic, and syndiotactic polypropylene polymers, and propylene copolymers such as propylene random, block or impact copolymers. In addition, polymers of polyethylene include high density polyethylene (HDPE), mixtures with other olefins such as polypropylene with polyethylene (for example PP/HDPE, PP/LDPE) and mixtures of different types of polyethylene (for example LDPE/HDPE), may also be used. Also useful are copolymers of monoolefins and diolefins with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidene-norbornene; as well as mixtures of such copolymers and their mixtures with polymers mentioned above, for example polypropylene/ethylene propylene-copolymers, LDPE/EVA, LDPE/EAA, LLDPE/EVA, and LLDPE/EAA. As one skilled in the art would readily appreciate, the polyethylene polymers used herein. e.g., LLDPE, can contain various comonomers such as, for example, 1-butene, 1-hexene and 1-octene comonomers.

The polymers used in combination with stabilizing compositions of the present invention are produced using a variety of polymerization processes including solution, high-pressure, slurry and gas phase using free radical polymerization or various catalysts including, for example, Ziegler-Natta, single-site, metallocene. Phillips-type (chromium-based) catalysts, TNZ (DuPont) or Standard Oil Indiana. Polyethylene and/or polypropylene polymers may be produced by, for example, polymerization of olefins in the presence of Ziegler-Natta catalysts, optionally on supports such as, for example, MgCl$_2$, chromium salts and complexes thereof, silica, silica-alumina and the like. The olefin polymers may also be produced utilizing chromium catalysts or single site catalysts, e.g., metallocene catalysts such as, for example, cyclopentadiene complexes of metals such as Ti and Zr. Exemplary metallocene catalyst are described in U.S. Pat. Nos. 4,827,064, 4,892,851, 4,912,272, 5,012,020, 5,126,303, 5,296,434, 5,324,800, 5,731,254 6,706,828, and 6,858,767, the entire contents and disclosure of which are incorporated by reference.

In another embodiment, the polyethylene or polypropylene polymer may comprise a biodegradable polymer or compostable polymer. Biodegradable polymers are those in which the degradation results from the action of naturally occurring microorganisms, such as bacteria, fungi and algae. Compostable polymers undergoes degradation by biological processes during composting to yield CO$_2$, water, inorganic compounds and a biomass at a rate consistent with other compostable materials. Typically the biodegradable or compostable polymers are derived from plant sources and are synthetically produced. Examples of biodegradable or compostable polymers include poly(glycolic acid) (PGA), poly (lactic acid) (PLA), and co-polymers thereof. Biodegradable or compostable polymers may also be derived from a blend of starch of a plant and a conventional petroleum-based polymer. For example, the biodegradable polymer may be blended with a polyolefin.

Although several polyethylenes and polypropylenes are described as within the scope of the present invention, in one embodiment, the polymer is linear-low density polyethylene (LLDPE) that is an ethylene-hexene or ethylene-octene copolymer having a density of 0.88 to 0.94 g/cc, e.g., from 0.9 to 9.4 g/cc or from 0.91 to 9.4 g/cc and melt flow index of from 0.3 to 150 g per 10 min, e.g., from 0.6 to 15 g per 10 min or from 0.8 to 3 g per 10 min. In one embodiment the LLDPE is produced with a metallocene catalyst (mLLDPE). In one embodiment the LLDPE has a wide molecular weight distribution of from 2.8 to 8.

B. Stabilizing Compositions

The stabilizing compositions of the present invention generally comprise a sterically hindered phenol and a phosphite, preferably a liquid phosphite. As discussed above, a stabilizing amount or effective amount of the sterically hindered phenol and liquid phosphite compositions of the invention may be used as stabilizers for various types of polymer resins. As used herein, by "stabilizing amount" and an "effective amount" it is meant when the polymer resins containing the stabilizing composition of the invention shows improved stability in any of its physical or color properties in comparison to an analogous polymer composition that does not include a stabilizing composition of the invention. Examples of improved stability include improved stabilization against, for example, molecular weight degradation, color degradation, and the like from, for example, melt processing, weathering, and/or long term field exposure to air, heat, light, and/or other elements. In one example, improved stability is obtained in the form of one or both of lower initial color as measured by yellowing index (YI) and/or melt flow rate of the molten polymer or additional resistance to weathering, as measured, for example, by initial yellowing index, or by resistance to yellowing and change in color, when compared to a polymer without the stabilizer additives or a polymer with a conventional stabilizer. In one example, the improved stability is measured by low gel content, no black specs, and/or improved screen pack plugging.

In one embodiment, the stabilizing composition is added to the polymer in an amount from 250 to 5000 wppm, e.g., from 300 to 3000 wppm or from 800 to 2600 wppm. The weight ratio of sterically hindered phenol to phosphite may be from 1:1 to 1:20, e.g., from 1:3 to 1:15 or from 1:5 to 1:12. Although conventional stabilizing compositions use more phenol or equivalent amounts of phenol and phosphites, in one embodiment of the present invention, the amount of sterically hindered phenol may be reduced such that the weight ratio is from 1:10 to 1:20, e.g., from 1:12 to 1:18 or from 1:12 to 1:15.

1. Sterically Hindered Phenolics

The sterically hindered phenols employed in the present invention generally have two or more hydroxyl groups, e.g., three or more hydroxyl groups. In one embodiment, the sterically hindered phenol has the structure as shown in compound I:

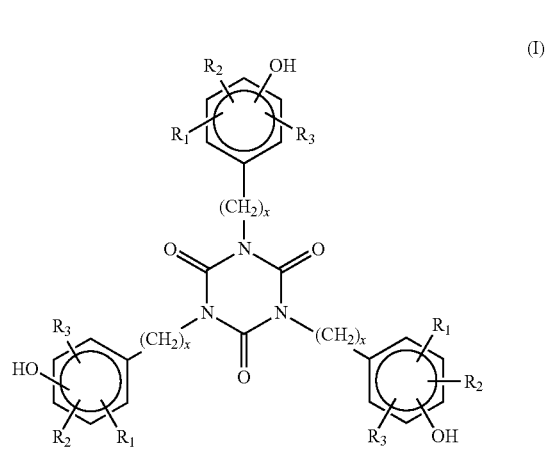

In another embodiment, the sterically hindered phenol has the structure as shown in compound II:

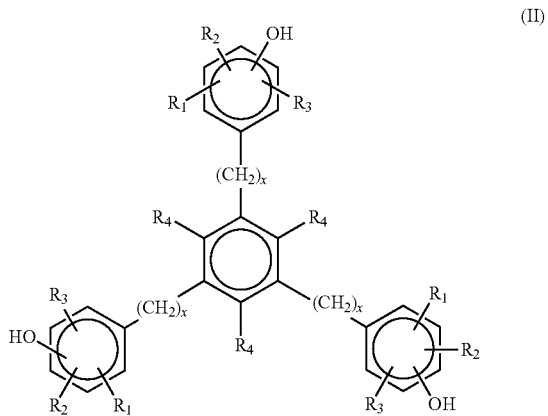

wherein: x is independently 0, 1, 2, or 3; $R_1$, $R_2$, and $R_3$ is independently hydrogen, $C_1$-$C_{12}$ alkyl, and $C_5$-$C_{10}$ cycloalkyl, provided that at least one of $R_1$, $R_2$, and $R_3$ is not hydrogen; and $R_4$ is independently $C_1$-$C_6$ alkyl. Preferably x is either 0 or 1. In one embodiment, at least one of $R_1$, $R_2$, and $R_3$ is a branched $C_3$-$C_6$ alkyl, e.g., branched butyl group or branched pentyl group. In one embodiment, at least one of $R_1$, $R_2$, and $R_3$ is methyl.

Suitable sterically hindered phenols of compound I include 1,3,5-tris-(4-tert-butyl-3-hydroxy-2,6-dimethylbenzyl)isocyanurate, 1,3,5-tris-(3,5-dicyclohexyl-4-hydroxybenzyl) isocyanurate, 1,3,5-tris-(3,5-di-tert-butyl-4-hydroxybenzyl) isocyanurate commercially available as Anox™ IC-14 (Chemtura) also available as Irganox™ 3114 (Ciba), and 1,3,5-tris(4-t-butyl-3-hydroxy-2,6-dimethylbenzyl)-1,3,5-Triazine-2,4,6-(1H,3H,5H)-trione commercially available as Lowinox™ 1790 (Chemtura) also available as Cyanox™ 1790 (Cytec Industries).

Suitable sterically hindered phenols of compound II include 1,3,5-tris-(3,5-di-tert-butyl-4-hydroxybenzyl)-2,4,6-trimethylbenzene commercially available as Anox™ 330 (Chemtura) and also available as Irganox™ 1330 (Ciba) and Ethanox™ 330 (Albemale).

2. Phosphites

There are several different types of phosphites or phosphonites that may be combined with the sterically hindered phenols discussed above, e.g., compound I or II. In one embodiment the phosphite or phosphonite is a liquid. Phosphite performance may be affected by phosphorous content, hydrolytic stability, polymer compatibility, solubility, and loading level.

a. Generally

In one embodiment, the phosphite or phosphonite, for example, may be selected from a triphenyl phosphite, diphenylalkyl phosphite, phenyldialkyl phosphite, tris(nonyl-phenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphites tristearyl sorbitol triphosphite, bis(2,4-dicumylphenyl)pentaerythritol diphosphite, tetrakis(2,4-di-tert-butylphenyl)-4,4'-biphenylene diphosphonites or mixtures thereof. Specific suitable phosphite compounds include triphenyl phosphite, tris(nonyl-phenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, tristearyl sorbitol triphosphite, tris(dipropyleneglycol)phosphite, tetrakis(2,4-di-tert-butylphenyl)-4,4'-biphenylene diphosphonite, and mixtures thereof. Suitable commercially available phosphites include, for example, Naugalube™ TPP, Naugalube TPP, Alkanox™ 240, Ultranox™ 626, Naugard P, Weston™ 399, Weston TNPP, Weston 430, Weston 618F, Weston 619F, Weston DPDP, Weston DPP, Weston PDDP, Weston PTP, Weston TDP, Weston TLP, Weston TPP, and Weston TLTTP (trilauryl trithio phosphite) made by Chemtura Corporation; Doverphos™ 4, Doverphos 4-HR, Doverphos 4-HR Plus, Doverphos HiPure 4, and Doverphos S-9228 made by Dover Chemical; and Hostanox PEPQ made by Clariant Chemicals.

b. Liquid Phosphite Compositions

In another preferred embodiment, the phosphite is a liquid phosphite composition comprising at least two different phosphites, e.g., at least three different phosphites, or at least four different phosphites, selected from the group consisting of a tris(dialkylaryl)phosphite, a tris(monoalkylaryl)phosphite, a bis(dialkylaryl)monoalkylaryl phosphite, and a bis(monoalkylaryl)dialkylaryl phosphite, as described in co-pending U.S. application Ser. Nos. 11/787,531, 12/534,000, 12/534,010, 12/534,019, 12/534,025, 12/534,035, 12/534,051, and 12/534,043, and U.S. Provisional Application Nos. 61/230,658, 61/230,654 and 61/230,652, the entire contents and disclosures of which are hereby incorporated by reference. Commercially available liquid phosphite compositions include, for example. Weston™ 705 made by Chemtura Corporation.

In some preferred embodiments, the phosphite composition comprises at least two different phosphites having the structure of formula III.

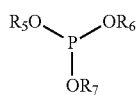

(III)

wherein $R_5$, $R_6$ and $R_7$ are independently selected alkylated aryl groups and wherein the liquid phosphite composition is a liquid at ambient conditions. By "ambient conditions" it is meant room temperature, e.g., 25° C., and 1 atmosphere pressure.

The aryl moiety present in the phosphites of the liquid phosphite composition is preferably an aromatic moiety of from 6 to 18 carbon atoms, e.g., phenyl, naphthyl, phenanthryl, anthracyl, biphenyl, terphenyl, o-cresyl, m-cresyl, p-cresyl, and the like, preferably phenyl. Each aromatic moiety is substituted with at least one $C_1$-$C_{18}$, e.g., $C_4$-$C_{10}$, or $C_4$-$C_5$ alkyl group. Preferably no aromatic moieties are substituted with any $C_9$ alkyl groups. The aromatic moieties may be mono-, di-, or tri-substituted in the ortho and/or para positions, but preferably the phosphites themselves are not exclusively mono-substituted, are not exclusively di-substituted, and are not exclusively tri-substituted.

In preferred embodiments, the invention is to a stabilized liquid phosphite composition comprising a liquid phosphite composition and an amine compound, wherein the liquid phosphite composition comprises at least two of a tris(dialkylaryl)monophosphate, a tris(monoalkylaryl)phosphite, a bis(dialkylaryl)monoalkylaryl phosphite, and a bis(monoalkylaryl)dialkylaryl phosphite, wherein the phosphite composition is a liquid at ambient conditions. Thus, the liquid phosphite composition comprises at least one phosphite that has at least one aromatic moiety that is multiply substituted, such as a bis(dialkylaryl)monoalkylaryl phosphite, a bis(monoalkylaryl)dialkylaryl phosphite, or a tris(dialkylaryl) phosphite. The liquid phosphite composition also preferably includes at least one phosphite compound in which each aryl moiety is entirely monosubstituted, e.g. a tris(monoalkylaryl) phosphite. The alkyl group in the alkylaryl phosphite compounds preferably comprises a $C_3$-$C_5$ alkyl group, e.g., a $C_4$-$C_5$ alkyl group, most preferably t-butyl and/or t-amyl, and the aryl group preferably comprises phenyl or cresyl, e.g., o-, m-, and/or p-cresyl.

More generally, the alkyl substituent(s) on the aryl moieties are selected from straight-chain or branched $C_1$-$C_{18}$ alkyl, e.g., $C_1$-$C_8$ alkyl, $C_4$-$C_6$, alkyl, or $C_4$-$C_5$ alkyl, preferably $C_4$ alkyl or $C_5$ alkyl. In a preferred embodiment, the alkyl substituent(s) is not $C_8$-$C_{10}$ alkyl, e.g., not $C_9$ alkyl. The alkyl substituent may include, for example, methyl, ethyl, propyl, butyl, amyl, hexyl, heptyl, octyl, nonyl (although less preferred), decyl, undecyl, dodecyl, tridecyl, tetradecyl, pentadecyl, hexadecyl, heptadecyl, octadecyl, and isomers thereof. Most preferably, the alkyl group(s) are selected from butyl (especially sec-butyl and/or tert-butyl) and amyl groups (especially sec-amyl, tert-amyl, and/or neo-amyl). As indicated above, in a preferred embodiment, the alkyl moieties do not include nonyl, meaning the phosphite composition preferably comprises less than 50 wppm, e.g., less than 10 wppm, or less than 5 wppm, nonyl substituted aryl phosphite compounds, and most preferably no detectable nonyl substituted aryl phosphite compounds. In addition, the phosphite composition preferably comprises less than 50 wppm, e.g., less than 10 wppm, or less than 5 wppm, nonylphenol. Most preferably, the phosphite composition comprises no detectable nonylphenol.

In one embodiment, the phosphite composition is substantially free of phosphite compounds having aryl groups that are substituted with alkyl groups having hydrogens in the α position. In preferred embodiments, at least 95%, at least 98%, or at least 99% of the aryl moieties are substituted with alkyl groups having tertiary α-carbons, e.g., tert-butyl and/or tert-amyl.

In one embodiment, $R_5$, $R_6$, and $R_7$ are independently selected alkylated aryl groups of the structure of formula (IV):

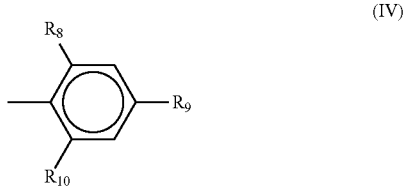

wherein $R_5$, $R_9$, and $R_{10}$ are independently selected from the group consisting of hydrogen and straight or branched $C_1$-$C_8$ alkyl, e.g., methyl, ethyl, propyl, butyl, amyl, hexyl, heptyl, octyl, and isomers thereof, e.g., isopropyl, tert-butyl, tert-amyl, neo-amyl, provided that at least one of $R_8$, $R_9$, and $R_{10}$ is not hydrogen. In one embodiment $R_8$ and $R_{10}$ are hydrogen, and $R_9$ is not hydrogen. In one embodiment, the ortho alkyl groups, e.g., $R_8$ and $R_{10}$, have no α-hydrogen atoms. In one embodiment, the ortho alkyl groups, e.g., $R_8$ and $R_{10}$, have tertiary α-carbon atoms selected from the group consisting of tert-butyl and tert-amyl.

In one embodiment, $R_8$ and $R_9$ are independently selected from the group consisting of methyl, ethyl, propyl, butyl, amyl, hexyl, and isomers thereof, and $R_{10}$ is hydrogen. In another embodiment, $R_8$ and $R_{10}$ are hydrogen and $R_9$ is independently selected from the group consisting of methyl, ethyl, propyl, butyl, amyl, hexyl, and isomers thereof. In one aspect of these embodiments, at least one of $R_8$, $R_9$, and $R_{10}$ are $C_4$ or $C_5$ alkyl, most preferably tert-butyl or tert-amyl.

In various optional embodiments, the alkylated aryl groups for $R_5$, $R_6$, and $R_7$ are provided as shown in Table 1. In some embodiments, the liquid phosphite composition, as described herein, may comprise any two or more of these compounds in amounts sufficient for the phosphite composition to be a liquid at ambient conditions.

TABLE 1

| | $R_5$ | | | $R_6$ | | | $R_7$ | | |
|---|---|---|---|---|---|---|---|---|---|
| # | $R_8$ | $R_9$ | $R_{10}$ | $R_8$ | $R_9$ | $R_{10}$ | $R_8$ | $R_9$ | $R_{10}$ |
| 1 | H | t-butyl | H | H | t-butyl | H | H | t-butyl | H |
| 2 | t-butyl | t-butyl | H | H | t-butyl | H | H | t-butyl | H |
| 3 | t-butyl | t-butyl | H | t-butyl | t-butyl | H | H | t-butyl | H |
| 4 | t-butyl | t-butyl | H | t-butyl | t-butyl | H | t-butyl | t-butyl | H |
| 5 | H | t-amyl | H | H | t-amyl | H | H | t-amyl | H |
| 6 | t-amyl | t-amyl | H | H | t-amyl | H | H | t-amyl | H |
| 7 | t-amyl | t-amyl | H | t-amyl | t-amyl | H | H | t-amyl | H |
| 8 | t-amyl | t-amyl | H | t-amyl | t-amyl | H | t-amyl | t-amyl | H |
| 9 | H | t-butyl | H | H | t-butyl | H | H | t-amyl | H |
| 10 | H | t-butyl | H | H | t-amyl | H | H | t-amyl | H |
| 11 | t-butyl | t-butyl | H | H | t-butyl | H | H | t-amyl | H |
| 12 | t-butyl | t-butyl | H | H | t-amyl | H | H | t-amyl | H |
| 13 | t-butyl | t-amyl | H | H | t-amyl | H | H | t-amyl | H |
| 14 | t-amyl | t-amyl | H | H | t-butyl | H | H | t-amyl | H |
| 15 | t-amyl | t-amyl | H | H | t-butyl | H | H | t-butyl | H |
| 16 | t-butyl | t-butyl | H | t-butyl | t-butyl | H | H | t-amyl | H |
| 17 | t-butyl | t-butyl | H | t-butyl | t-amyl | H | H | t-butyl | H |
| 18 | t-butyl | t-amyl | H | t-butyl | t-amyl | H | H | t-butyl | H |
| 19 | t-amyl | t-amyl | H | t-amyl | t-amyl | H | H | t-butyl | H |
| 20 | t-butyl | t-amyl | H | t-butyl | t-butyl | H | t-butyl | t-butyl | H |
| 21 | t-butyl | t-amyl | H | t-butyl | t-amyl | H | t-amyl | t-butyl | H |

In one embodiment, $R_5$, $R_6$, and $R_7$ are independently selected alkylated aryl groups of the structure of formula (V):

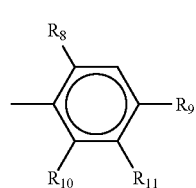

(V)

wherein $R_8$, $R_9$, and $R_{10}$ are defined above and $R_{11}$ is hydrogen or methyl, provided that one of $R_8$, $R_9$, $R_{10}$, and $R_{11}$ is methyl and that at least two of $R_8$, $R_9$, $R_{10}$, and $R_{11}$ are not hydrogen. Such phosphites may be formed, for example, by the reaction of one or more alkylated cresol compounds, e.g., one or more of alkylated ortho-, meta-, and/or para-cresol, with $PCl_3$.

In some preferred embodiments, the liquid phosphite composition comprises at least two phosphites selected from the group consisting of tris(4-t-butylphenyl)phosphite, tris(2-t-butylphenyl)phosphite, tris(2,4-di-t-butylphenyl)phosphite, bis(4-t-butylphenyl)-2,4-di-t-butylphenyl phosphite, bis(2,4-di-t-butylphenyl)-4-t-butylphenyl phosphite, bis(2-t-butylphenyl)-2,4-di-t-butylphenyl phosphite, bis(2,4-di-t-butylphenyl)-2-t-butylphenyl phosphite, tris(4-t-amylphenyl)phosphite, tris(2-t-amylphenyl)phosphite, tris(2,4-di-t-amylphenyl)phosphite, bis(4-t-amylphenyl)-2,4-di-t-amylphenyl phosphite, bis(2,4-di-t-amylphenyl)-4-tamylphenyl phosphite, bis(2-t-amylphenyl)-2,4-di-t-amylphenyl phosphite, and bis(2,4-di-t-amylphenyl)-2-tamylphenyl phosphite. In one embodiment, the phosphite composition does not comprise only phosphites that, when combined in a composition, would result in a solid composition. An example of a phosphite that would result in a solid composition is one produced from the reaction of 2,4-di-t-butylphenol and 2,4-di-t-amylphenol with phosphorus trichloride as described in U.S. Pat. No. 5,254,709.

In some embodiments, the phosphite composition has an overall phosphorus content that is equal to or greater than that of TNPP, e.g., at least 4.5 wt. %, e.g., at least 4.8 wt. %, or at least 5.1 wt. %. In terms of ranges, the overall phosphorus content of the phosphite composition may range, from 4.5 to 10.0 wt. %, e.g., from 4.8 to 8.0 wt. %, or 5.1 to 6.0 wt. %, based on the total weight of all phosphorous-containing compounds in the phosphite composition.

As indicated above, the phosphite composition preferably comprises at least two of the following: a tris(dialkylaryl) monophosphite, a tris(monoalkylaryl)phosphite, a bis(dialkylaryl)monoalkylaryl phosphite, and a bis(monoalkylaryl) dialkylaryl phosphite, wherein the phosphite composition is a liquid at ambient conditions. The relative amounts of the respective phosphite components contained in the phosphite composition may vary somewhat so long as the phosphite composition itself is a liquid at ambient conditions. Preferably, the phosphite composition comprises at least two of these compounds, at least three of these compounds, or all four of these compounds, in an amount greater than 80 wt. %, 90 wt. %, or 95 wt. %, based on the total weight of all phosphite compounds in the phosphite composition. Of course, a minor amount of other species, phosphite or non-phosphite, may be present, e.g., one or more of tris(2-tert-amylphenyl)phosphite, bis(2-tert-amylphenyl)-2,4-di-tert-amylphenyl phosphite, bis(2,4-di-tert-amylphenyl)-2-tert-amylphenyl phosphite, and the like.

The relative amounts of the respective phosphite components contained in the liquid phosphite composition, as described herein, may vary somewhat so long as the phosphite composition is a liquid at ambient conditions. In terms of ranges, for example, the phosphite composition comprises a tris(monoalkylaryl)phosphite, tris(4-t-amyl-phenyl)phosphite or tris(4-t-butyl-phenyl)phosphite, in an amount from 20 to 70 wt. %, e.g., from 15 to 55 wt. %, or from 37 to 54 wt. %, and a bis(monoalkylaryl)dialkylaryl phosphite, bis(4-t-amyl-phenyl)-2,4-di-t-amyl-phenyl)phosphite or bis(4-t-butyl-phenyl)-2,4-di-t-butyl-phenyl)phosphite, in an amount from 15 to 60 wt. %, e.g., from 31 to 50 wt. %, or from 34 to 45 wt. %. Optionally, the phosphite composition further comprises a tris(dialkylaryl)phosphite, and/or bis(dialkylaryl) monoaryl phosphite. If present, the tris(dialkylaryl)phosphite, e.g., tris(2,4-di-tert-amyl-phenyl)phosphite or tris(2,4-di-tert-butyl-phenyl)phosphite, preferably is present in an amount of from 0.1 to 20 wt. %, e.g., from 0.3 to 5 wt. %, or from 0.5 to 1 wt. %. If present, the bis(dialkylaryl)monoaryl phosphite, e.g., bis(2,4-di-tert-amyl-phenyl)-4-t-amyl-phenyl phosphite or bis(2,4-di-tert-butyl-phenyl)-4-t-butyl-phenyl phosphite, preferably is present in an amount of from 2 to 20 wt. %, e.g., from 4 to 20 wt. %, or from 5 to 10 wt. %. Unless otherwise indicated, weight percent (wt. %) is based on the total weight of the phosphite composition.

In terms of weight ratios, the phosphite composition optionally has a weight ratio of tris(monoalkylaryl)phosphites to the combination of bis(monoalkylaryl)dialkylaryl phosphites, bis(dialkylaryl)monoalkylaryl phosphites and tris(dialkylaryl)phosphites of from 1:4 to 7:3, e.g., from 2:5 to 3:2, or from 3:5 to 6:5.

The phosphite composition optionally has a weight ratio of bis(monoalkylaryl)dialkylaryl phosphites to the combination of tris(monoalkylaryl)phosphites, bis(dialkylaryl)monoalkylaryl phosphites and tris(dialkylaryl)phosphites of from 1:6 to 3:2 e.g., from 1:3 to 1:1, or from 1:2 to 2:3.

The phosphite composition optionally has a weight ratio of bis(dialkylaryl)monoalkylaryl phosphites to the combination of tris(monoalkylaryl)phosphites, bis(monoalkylaryl)dialkylaryl phosphites, and tris(dialkylaryl)phosphites of from 1:50 to 2:5, e.g., from 1:30 to 1:5, or from 1:20 to 1:9, or optionally less than 0.2:1, less than 0.1:1, less than 0.05:1, or less than 0.02:1.

The phosphite composition optionally has a weight ratio of tris(dialkylaryl)phosphites to the combination of bis (monoalkylaryl)dialkylaryl phosphites, bis(dialkylaryl) monoalkylaryl phosphites and tris(monoalkylaryl)phosphites of from 1:10,000 to 2:5, e.g., from 1:5,000 to 1:20, or from 1:1,000 to 1:100, or optionally less than 0.02:1, less than 0.01:1, or less than 0.005:1.

Preferably, the liquid phosphite composition comprises at least two of a tris(di-$C_3$-$C_5$ alkylaryl)phosphite, a tris($C_3$-$C_5$ alkylaryl)phosphite, a bis(di-$C_3$-$C_5$ alkylaryl) $C_3$-$C_5$ alkylaryl phosphite, and a bis($C_3$-$C_5$ alkylaryl)di-$C_3$-$C_5$ alkylaryl phosphite. Preferably the composition comprises each of the these phosphites in the following amounts: 1-5 wt % of the tris(di-$C_3$-$C_5$ alkylaryl)phosphite, 10-70 wt % of the tris($C_3$-$C_5$ alkylaryl)phosphite, 1-35 wt % of the bis(di-$C_3$-$C_5$ alkylaryl) $C_3$-$C_5$ alkylaryl phosphite, and 5-70 wt % of the bis($C_3$-$C_5$ alkylaryl)di-($C_3$-$C_5$ alkylaryl phosphite.

As suggested above, the liquid phosphite compositions may be characterized based on how the aryl moieties, e.g., phenyl moieties, are substituted, e.g., alkyl (e.g., t-butyl or t-amyl) substituted, as a whole. For example, in one embodiment, a majority of the aryl moieties are mono substituted in the para-position, e.g., at least 50%, at least 70%, or at least 90% mono substituted in the para-position, optionally from 50 to 95%, e.g., from 55 to 90, or from 60 to 85% mono substituted in the para-position, based on the number of aryl moieties in the phosphite composition. In other embodiments, some of the aryl moieties are disubstituted, e.g., ortho- and para-disubstituted, at least in part. Preferably at least 10% of the aryl moieties are ortho- and para-disubstituted, e.g., at least 20% ortho- and para-disubstituted, or at least 50% ortho- and para-disubstituted, optionally from 5 to 50% ortho- and para-disubstituted, e.g., from 10 to 45% ortho- and para-disubstituted, or from 15 to 40% ortho- and para-disubstituted, based on the total number of aryl moieties in the phosphite composition. In other embodiments, the ratio of monoalkylaryl groups to dialkylaryl groups ranges from 5:1 to 1:1, e.g., from 4:1 to 1:1, or from 3.5:1 to 2:1.

Depending largely on how the phosphites are manufactured, the phosphite compounds may be similarly substituted on each aryl moiety per molecule, e.g., some phosphite compounds may be exclusively monosubstituted, e.g., para-substituted, and/or some phosphite compounds may be exclusively disubstituted, e.g., ortho and para disubstituted, provided that at least some portion of the aryl moieties in the overall phosphite composition are mono-substituted and at least some portion of the aryl moieties in the overall phosphite composition are disubstituted. For example, some or all of the phosphite molecules may contain both mono and disubstituted aryl moieties. Additionally or alternatively, the phosphite composition may comprise phosphite molecules that are exclusively monosubstituted, e.g., para substituted and/or phosphite molecules that are exclusively disubstituted, e.g., o/p disubstituted.

As indicated above, the liquid phosphite composition, as described herein, includes phosphite compounds having aryl moieties that are monoalkylated and dialkylated. Ideally, few if any of the aryl moieties are trisubstituted. For example, fewer than 3 wt. % of the aryl moieties are trisubstituted, e.g., fewer than 2 wt. %, or fewer than 1 wt. %.

Similarly, it is preferred that few, if any, of the aryl moieties are monosubstituted in the ortho position. Preferably, the aryl moieties are monosubstituted in the ortho position, if at all, in an amount less than 3 wt. %, e.g., less than 2 wt. %, or less than 1 wt. %.

Preferably, the phosphite composition has a low level or is substantially free of phenolics (e.g., phenols, cresols or xylenols), whether alkylated or unalkylated, which are referred to herein as "free phenolics" when contained in the phosphite composition. In terms of amounts, the phosphite composition preferably comprises less than 5 wt. %, e.g., less than 3 wt. %, or less than 1 wt. %, of free phenolics, based on the total weight of the phosphite composition. Any free phenolics, for example, may be removed by distillation. Extremely low levels of free phenolics may be achieved, for example, by employing a wiped-film molecular (Short-Path) still, wiped film evaporator (WFE), thin film evaporator, or similar equipment. In terms of amounts, the phosphite composition may comprise less than 0.5 wt. %, e.g., less than 0.2 wt. %, or less than 0.1 wt. %, of free phenolics, based on the total weight of the phosphite composition.

In other cases, a minor amount of free phenolics may be beneficial, for example, as a viscosity reducing agent. Thus, the phosphite composition may comprise a minor amount of free phenolics, e.g., from 1 to 4 weight percent, e.g., from 2 to 3 weight percent, based on the total weight of the phosphite composition.

In addition, the phosphite composition is preferably substantially free of phosphite compounds having unsubstituted aryl moieties, e.g., triphenylphosphites, bis(phenyl)alkylphenyl phosphites, or bis(alkylphenyl)phenyl phosphites. In terms of amounts, the phosphite composition preferably comprises less than 2 wt. %, e.g., less than 1 wt. %, or less than 0.5 wt. %, phosphite compounds having at least one unsubstituted aryl moiety, based on the total weight of the phosphite composition.

As indicated above, the phosphite composition is a liquid at ambient conditions. As used herein, by "liquid," it is meant that the phosphite composition remains liquid after at least three "freeze/thaw" cycles as opposed to "meta-stable liquids," which do not remain liquid after three or fewer cycles. A freeze/thaw cycle is defined as follows: 1) An ambient temperature composition is stirred for 0.5 hours; 2) The stirred composition is then refrigerated at about 5° C. for three days; and 3) The refrigerated composition is then brought to ambient temperature and held at ambient for 3 days. Upon completion of step 3, the composition is checked for solids content, e.g., crystallization. Completion of steps 1-3 defines one freeze/thaw cycle.

As noted above, one feature of the phosphite composition is that it is in liquid physical form at room temperature. This is clearly surprising, given that the prior art teaches several examples of solid phosphite compositions, the components of which are separately solids at ambient condition, (See JP 59030842; WO 9303092; CA 2,464,551). In contrast, the phosphite composition discussed herein is liquid even though the individual components are solid. Table 2 provides the melting points of several different individual phosphite compounds that may be included in the stabilized phosphite composition.

TABLE 2

| Phosphite | Melting Point |
|---|---|
| tris(4-tert-butylphenyl)phosphite | 75-76° C. |
| tris(2,4-di-tert-butylphenyl)phosphite | 181-184° C. |
| bis(4-tert-butylphenyl)-2,4-di-tert-butylphenyl phosphite | 63-65° C. |
| bis(2,4-di-tert-butylphenyl)-4-tert-butylphenyl phosphite | 100-103° C. |
| tris(4-tert-amylphenyl)phosphite | 52-54° C. |
| tris(2,4-di-tert-amylphenyl)phosphite | 103° C. |

The viscosity of the phosphite composition may vary depending on the relative amounts of the various phosphite compounds contained therein. In some exemplary embodiments, the phosphite composition has a viscosity less than 11,000 cSt, e.g., less than 7,300 cSt, less than 5,000 cSt, less than 3,000 cSt, or less than 2850 cSt, these viscosities being measured at 30° C. In terms of ranges, viscosity of the composition may range from 1 cSt to 15,000 cSt, from 100 cSt to 12,000 cSt, from 500 cSt to 10,000 cSt, from 500 cSt to 6,500 cSt, from 500 cSt to 5,000 cSt, from 500 cSt to 3,000 cSt, from 1,000 cSt to 4,000 cSt, from 1.500 cSt to 3,500 cSt, from 2,000 cSt to 3.000 cSt, or from 2,000 to 2,800 cSt, these viscosities being measured at 30° C.

In one embodiment, the liquid phosphites, including the phosphite composition includes one or more hydrolytic stabilizers. Suitable hydrolytic stabilizers include triethanolamine, triisopropanolamine, diethanolamine, diisopropanolamine, and tetraisopropanolethylenediamine.

In another aspect the hydrolytic stabilizers include octyl-bis(2-ethanol)amine, nonyl-bis(2-ethanol)amine, decyl-bis(2-ethanolamine, undecyl-bis(2-ethanol)amine, dodecyl-bis(2-ethanol)amine, tridecyl-bis(2-ethanol)amine, tetradecyl-bis(2-ethanol)amine, pentadecyl-bis(2-ethanol)amine, hexadecyl-bis(2-ethanol)amine, heptadecyl-bis(2-ethanol)amine, octadecyl-bis(2-ethanol)amine, octyl-bis(2-propanol)amine, nonyl-bis(2-propanol)amine, decyl-bis(2-propanol)amine, undecyl-bis(2-propanol)amine, dodecyl-bis(2- propanol)amine, tridecyl-bis(2-propanol)amine, tetradecyl-bis(2-propanol)amine, pentadecyl-bis(2-propanol)amine, hexadecyl-bis(2-propanol)amine, heptadecyl-bis(2-propanol)amine, octadecyl-bis(2-propanol)amine, and isomers thereof. Commercially available hydrolytic stabilizers include Armostat™ 300 and Armostat 1800 manufactured by Akzo Nobel Polymers. Additional hydrolytic stabilizers include epoxies such as epoxidized soybean oil (ESBO) commercially available as Drapex™ 39, Drapex 392, Drapex 4.4, and Drapex 6.8 (Chemtura Corp.).

C. Other Liquid Phosphites

In yet another one embodiment, the phosphite is a liquid tris(mono-alkyl)phenyl phosphite ester or a liquid mixture of liquid tris(mono-alkyl)phenyl phosphite esters, as described in U.S. Pat. No. 7,468,410, the entire contents and disclosures of which are hereby incorporated by reference. In particular, the phosphite may be tris(3-t-butylphenyl)phosphite, tris(2-sec-butylphenyl)phosphite, or tris(4-sec-butylphenyl)phosphite. In one embodiment, the liquid mixture comprises different phosphites, one of which is tris(3-t-butylphenyl)phosphite, tris(2-sec-butylphenyl)phosphite, or tris(4-sec-butylphenyl)phosphite and the other of which is tris(3-t-butylphenyl)phosphite, tris(2-sec-butylphenyl)phosphite, tris(4-sec-butylphenyl)phosphite, tris(2-t-butylphenyl)phosphite, tris(4-t-butylphenyl)phosphite, or tris(2,4-di-t-butylphenyl)phosphite.

3. Other Additives

In addition to the sterically hindered phenol and the phosphite, there may be one or more additives and stabilizers that are preferably present in an amount effective to improve composition stability. The one or more additives and stabilizers include additional phenolic antioxidants, aromatic amines, hydroxylamines, alkylamine-N-oxides, lactones, and thioethers, hindered amine light stabilizers (HALS), the ultraviolet light absorbers, alkaline metal salts of fatty acids, hydrotalcites, metal oxides, epoxydized soybean oils, the hydroxylamines, the tertiary amine oxides, lactones, thermal reaction products of tertiary amine oxides, and the thiosynergists. In one embodiment, the total amount of additives, including the sterically hindered phenol and the liquid phosphite, may from 0.025 wt % to 20 wt %, e.g., from 0.1 to 5 wt %, or from 0.3 to 3 wt %, based on the total weight the polymer and additives.

In one embodiment, the amount of each component in the stabilizing composition, based on the total weight percent of the polymer, is shown in Table 3.

TABLE 3

| Component | Range | Preferred Range |
|---|---|---|
| Stabilizers of Present Invention | 0.025-0.5 wt % | 0.08-0.26 wt % |
| Additional Phenolic Antioxidants | 0-3.0 wt % | 0.001-2.0 wt % |
| UV or light stabilizers | 0-3.0 wt % | 0.001-2.0 wt % |
| Metal deactivators | 0-3.0 wt % | 0.001-2.0 wt % |
| Peroxide scavengers | 0-3.0 wt % | 0.001-2.0 wt % |
| Polyamide stabilizers | 0-3.0 wt % | 0.001-2.0 wt % |
| Basic co-stabilizers | 0-3.0 wt % | 0.001-2.0 wt % |
| Nucleating and clarifying agents | 0-3.0 wt % | 0.001-2.0 wt % |
| Aminoxy propanoate | 0-3.0 wt % | 0.001-2.0 wt % |

The stabilizer compositions of the invention or the resulting stabilized polymer compositions optionally also comprise additional phenolic antioxidants that are blended or mixed with the sterically hindered phenols of the present invention. The additional phenolic antioxidants include the following:

(i) Alkylated monophenols, for example: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2,6-bis(α-methylbenzyl)-4-methylphenol, 2-(α-methylcyclohexyl)-4,6-dimethylphenol, 2,6-dioctadecyl-4-methylphenol, 2,4,6.-tricyclohexylphenol, and 2,6-di-tert-butyl-4-methoxymethylphenol. Commercially available alkylated monophenols include Lowinox™ 624 and Naugard™ 431 made by Chemtura Corp. Other phenols are commercially available as BHEB from Nanjing Datang Chemical Co., Ltd.

(ii) Alkylated hydroquinones, for example, 2,6-di-tert-butyl-4-methoxyphenol, tert-butyl-hydroquinone, 2,5-di-tert-amyl-hydroquinone, and 2,6-diphenyl-4-octadecyloxyphenol. Commercially available alkylated hydroquinones include Lowinox AH25 made by Chemtura.

(iii) Hydroxylated thiodiphenyl ethers, for example, 2,2'-thio-bis-(6-tert-butyl-4-methylphenol), 2,2'-thio-bis-(4-octylphenol), 4,4'-thio-bis-(6-tert-butyl-3-methylphenol), and 4,4'-thio-bis-(6-tert-butyl-2-methylphenol). Commercially available hydroxylated thiodiphenyl ethers include Lowinox TMB6, and Lowinox TBP6 made by Chemtura.

(iv) Alkylidene-bisphenols, for example, 22'-methylene-his-(6-tert-butyl-4-methylphenol), 2,2'-methylene-bis-(6-tert-butyl-4-ethylphenol), 2,2'-methylene-bis-(4-methyl-6-(α-methylcyclohexyl)phenol), 2,2'-methylene-bis-(4-methyl-6-cyclohexylphenol), 2,2'-methylene-bis-(6-nonyl-4-methylphenol), 2,2'-methylene-bis-(6-nonyl-4-methylphenol), 2,2'-methylene-bis-(6-(α-methylbenzyl)-4-nonylphenol), 2,2'-methylene-bis-(6-(alpha,alpha-dimethylbenzyl)-4-nonyl-phenol), 2,2'-methylene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenol)butane, 1,1-bis(2-methyl-4-hydroxy-5-tert-butylphenyl)butane, 2,2'-isobutylidene-bis(4,6-dimethylphenol), 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-dodecyl-mercaptobutane, ethyleneglycol-bis-(3,3,-bis-(3'-tert-butyl-4'-hydroxyphenyl)-butyrate)-di-(3-tert-butyl-4-hydroxy-5-methylphenyl)-dicyclopentadiene, and di-(2-(3"-tert-butyl-2'hydroxy-5'methyl-benzyl)-6-tert-butyl-4-methylphenyl)terephthalate. Commercially available alkylidene-bisphenols include Lowinox 22IB46, Lowinox WSP, Lowinox 44B25. Naugard 536. Naugawhite™, and Lowinox 22IB46 made by Chemtura.

(v) Acylaminophenols, for example, 4-hydroxylauric acid anilide, 4-hydroxy-stearic acid amilide, 2,4-bis-octylmercapto-6-(3,5-tert-butyl-4-hydroxyanilino)-s-triazine, and octyl-N-(3,5-di-tert-butyl-4-hydroxyphenyl)-carbamate.

(vi) Esters of beta-(3,5-di-tert-butyl-4-hydroxyphenol)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethylisocyanurate, thiodiethyleneglycol, di-hydroxyethyl oxalic acid diamide. Such phenols also include tetrakis[methylene{3,5-di-tert-butyl-4-hydroxycinnamate}] methane. Commercially available esters include Anox 20, Anox 1315, Lowinox GP45, Naugalube 38, Naugalube 531, Anox PP18, Naugard PS48 and Naugard XL-1 made by Chemtura.

(vii) Thio esters of beta-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, dihydroxyethyl oxalic acid diamide. Commercially available thio esters include Naugalube™ 15 and Anox 70 made by Chemtura.

(viii) Amides of beta-(3,5-di-tert-butyl-4-hydroxyphenol)-propionic acid for example, N,N'-di-(3,5-di-tert-butyl-4-hydroxyphenylpropionyl)-hexammethylen-diamine N,N'-di-(3,5-di-tert-butyl-4-hydroxyphenylpropienyl) trimethylenediamine, N,N'-di-(3,5-di-tert-butyl-4-hydroxyphenylpropionyl)-hydrazine, N,N'-Hexamethylene bis[3-(3,5-di-t-butyl-4-hydroxyphenyl)propionamide, and 1,2-Bis(3,5-di-tert-butyl-4-hydroxyhydrocinnamoyl)hydrazine. Commercially available amides include Lowinox HD98 and Lowinox MD24 made by Chemtura.

(ix) Other phenolic antioxidants include the following phenols. Polymeric phenols such as the reaction product of 4-methylphenol with dicyclopentadiene and isobutylene, commercially available as Lowinox CSTL; Chemtura. Alkylidenepoly-phenols, such as 1,3 tris(3-methyl-4-hydroxyl-5-t-butyl-phenyl)-butane (Lowinox CA22; Chemtura). Thio phenols such as 2,6-di-tert-butyl-4-(4,6-bis(octylthio)-1,3,5-triazin-2-ylamino)phenol (Irganox™ 565; Ciba), 4,6-bis(octylthiomethyl)-o-cresol (Irganox 1520; Ciba); 4,6-bis(dodecylthiomethyl)-o-cresol (Irganox 1726; Ciba). Hydroxyl amines, such as bis(octadecyl)hydroxylamine (Irgastab™ FS 042; Ciba). Ester phenols include bis[3,3-bis(4-hydroxy-3-tert-butyl phenyl)butanoic acid]glycol ester (Hostanox™ O3; Clariant Chemicals). Still other phenols include 2-[1-(2-hydroxy-3,5-di-tert-pentylphenyl)ethyl]-4,6-di-tert-pentylphenyl acrylate (Sumilizer GS; Sumitomo Chemical).

The stabilizer compositions and/or the resulting stabilized polymer compositions optionally also comprise one or more UV absorbers and/or light stabilizers, such as the following:

(i) 2-(2'-hydroxyphenyl)-benzotriazoles, for example, the 5'-methyl-, 3'5'-di-tert-butyl-, 3'5'-di-tert-amyl-, 5'-tert-butyl-, 5'-tert-amyl-, 5'(1,1,3,3-tetramethylbutyl)-, 5-chloro-3', 5'-di-tert-butyl-, 5-chloro-3'-tert-butyl-5'methyl-, 3'-sec-butyl-5'tert-butyl-4'-octoxy, 3',5'-ditert-amyl-3'5'-bis-(α,α-dimethylbenzyl)-derivatives. Commercially available 2-(2'-hydroxyphenyl)-benzotriazoles include Lowilite™ 26, Lowilite 27, Lowilite 28, Lowilite 29, Lowilite 35, Lowilite 55, and Lowilite 234 made by Chemtura.

(ii) 2-Hydroxy-benzophenones, for example, the 4-hydroxy, 4-methoxy-, 4-octoxy, 4-decyloxy-, 4-dodecyloxy-, 4-benzyloxy-, 2,4-dihydroxy-, 4,2',4'-trihydroxy- and 2'-hydroxy-4,4'-dimethoxy-derivative. Exemplary 2-hydroxy-benzophenones include 2-hydroxy-4-methoxybenzophenone, 2-hydroxy-4-ethoxybenzophenone, 2,4-dihydroxybenzophenone, and 2-hydroxy-4-propoxybenzophenone. Commercially available 2-(2'-hydroxyphenyl)-benzotriazoles include Lowilite 20, Lowilite 22, Lowilite 20S, and Lowilite 24 made by Chemtura.

(iii) Esters of substituted and unsubstituted benzoic acids for example, phenyl salicylate, 4-tert-butylphenyl-salicilate, octylphenyl salicylate, dibenzoylresorcinol, bis-(4-tert-butylbenzoyl)-resorcinol, benzoylresorcinol, 2,4-di-tert-butyl-phenyl-3,5-di-tert-butyl-4-hydroxybenzoate and hexadecyl-3,5-di-tert-butyl-4-hydroxybenzoate.

(iv) UV absorbers and light stabilizers may also comprise acrylates, for example, alpha-cyano-beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)-2-methyl-indoline.

(v) Nickel compounds are also suitable UV absorbers and light stabilizers. Exemplary nickel compounds include nickel complexes of 2,2'-thio-bis(4-(1,1,1,3-tetramethylbutyl)-phenol), such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands. Commercially available nickel compounds include Lowilite Q84 (2,2'-Thiobis(4-tert-octyl-phenolato))-N-butylamine-Nichel(II) made by Chemtura.

(vi) Sterically hindered amines may be used as UV absorbers and light stabilizers. Sterically hindered amines, for example bis(2,2,6,6-tetramethylpiperidyl)-sebacate, his-(1,2,2,6,6-pentamethylpiperidyl)-sebacate. n-butyl-3,5-di-tert-butyl-4-hydroxybenzyl malonic acid bis(1,2,2,6,6-pentamethylpiperidyl)ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylenediamine and 4-tert-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetra-carbonic acid, 1,1'(1,2-ethanediyl)-bis-(3,3,5,5-tetramethyl piperazinone). Such amines include hydroxylamines derived from hindered amines, such as di(1-hydroxy-2,2,6,6-tetramethylpiperidin-4-yl)sebacate: 1-hydroxy 2,2,6,6-tetramethyl-4-benzoxypiperidine; 1-hydroxy-2,2,6,6-tetramethyl-4-(3,5-di-tert-butyl-4-hydroxy hydrocinnamoyloxy)-piperidine; and N-(1-hydroxy-2,2,6,6-tetramethyl-piperidin-4-yl)-epsiloncaprolactam. Commercially available hindered amines include Lowilite 19, Lowilite 62, Lowilite 77, Lowilite 92 and Lowilite 94 made by Chemtura.

(vii) Oxalic acid diamides, for examples, 4,4'-dioctyloxy-oxanilide, 2,2'-di-octyloxy-5',5'-di-tert-butyloxanilide, 2,2'-di-dodecyloxy-5',5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'ethyl-5,4-di-tert-butyloxanilide and mixtures of o- and p-methoxy—as well as of o- and p-ethoxy-disubstituted oxanilides.

The polymer resins and phosphite compositions of the invention may also include one or more additional additives, including, for example, one or more of the following:

(i) Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydrophenylpropionyl)-hydrazine, salicyloylamino-1,2,4-triazole, bis-benzyliden-oxalic acid dihydrazide.

(ii) Peroxide scavengers, for example, esters of betathiodipropionic acid, for example the lauryl, stearyl, myristyl or tridecyl esters, mercaptobenzimidazole or the zinc salt of 2-mercaptobenzimidazole, zinc-dibutyldithiocarbamate, dioctadecyldisulfide, pentaerythritoltetrakis-(beta-dodecylmercapto)-propionate.

(iii) Polyamide stabilizers, for example copper salts in combination with iodides and/or phosphorus compounds and salts of divalent manganese may also be included in the polymer resin and/or phosphite composition.

(iv) Basic co-stabilizers, for example, melamine, polyvinylpyrrolidone, dicyandiamide, triallyl cyanurate, urea derivatives, hydrazine derivatives, amines, polyamides, polyurethanes, hydrotalcites, alkali metal salts and alkaline earth metal salts of higher fatty acids, for example, Ca stearate, calcium stearoyl lactate, calcium lactate, Zn stearate, Zn octoate, Mg stearate, Na ricinoleate and K palmirate, antimony pyrocatecholate or zinc pyrocatecholate. Commercially available co-stabilizers include Mark™ 6045, Mark 6045ACM, Mark 6055, Mark 6055ACM, Mark 6087ACM, Mark 6102, Mark CE 345, Mark CE 350, and Mark CE 387, made by Chemtura; and DHT-4A™ made by Kisuma Chemicals.

(v) Nucleating and clarifying agents, for example, metal salts of 4-tert butylbenzoic acid, adipic acid, diphenylacetic acid, sorbitol and derivatives thereof, sodium benzoate, and benzoic acid.

(vi) Aminoxy propanoate derivatives such as methyl-3-(N, N-dibenzylaminoxy)propanoate; ethyl-3-(N,N-dibenzylaminoxy)propanonoate; 1,6-hexamethylene-bis(3-N,N-dibenzylaminoxy)proponoate); methyl-(2-(methyl)-3(N,N-dibenzylaminoxy)propanoate); octadecyl-3-(N,N-dibenzylaminoxy)propanoic acid; tetrakis (N,N-dibenzylaminoxy)ethyl carbonyl oxymethy)methane; octadecyl-3-(N,N-diethylaminoxy)-propanoate; 3-(N,N-dibenzylaminoxy)propanoic acid potassium salt; and 1,6-hexamethylene bis(3-(N-allyl-N-dodecyl aminoxy)propanoate).

(vii) Other additives, for example, plasticizers, lubricants, emulsifiers, pigments, optical brighteners, flameproofing agents, anti-static agents, blowing agents and thiosynergists such as dilaurylthiodipropionate or distearylthiodipropionate.

In one embodiment, the stabilizing composition of the present invention is substantially free of anti-gel agents, such as polyethylene glycols/oxides or ethoxylated linear alcohols, and contains less than 5 wppm of anti-gel agents or less than 2 wppm of anti-gel agents or no anti-gel agents. As used herein, anti-gel agents are those compounds added to the stabilizer mixture to reduce gel formation and does not include the stabilizing compositions of sterically hindered phenols and phosphites of the present invention.

Optionally in the polymer or polymeric resins there may also be from 5-50 wt %, e.g., 10-40 wt % or 15-30 wt % of fillers and reinforcing agents, for example, calcium carbonate, silicates, glass fibers, asbestos, talc, kaolin, mica, barium sulfate, metal oxides and hydroxides, carbon black and graphite.

C. Applications

Polymers that are stabilized with a stabilizing composition comprising a sterically hindered phenol and a liquid phosphite are useful in forming operations such as film, sheet, and fiber extrusion and co-extrusion as well as blow molding, injection molding and rotary molding. Films include blown or cast films formed by co-extrusion or by lamination useful as shrink film, cling film, stretch film, sealing films, oriented films, snack packaging, heavy duty bags, grocery sacks, general purpose bags, carrier bags, food packaging films, baked and frozen food packaging, agriculture films, medical packaging, industrial liners, or membranes, in food-contact or non-food contact applications. Fibers, such as those prepared by melt spinning, solution spinning and melt blown fiber operations, are used in woven or non-woven form to make filters, diaper fabrics, medical garments, geotextiles, etc. Extruded articles include, for example, medical tubing, wire and cable coatings, geomembranes, and pond liners. Molded articles include single and multi-layered constructions in the form of bottles, tanks, large hollow articles, rigid food containers and toys, etc. In addition to the above, the stabilizer compositions may be used in various rubber based products such as tires, barriers and the like.

D. Improved Performance Characteristics

When the stabilizer compositions of the invention are incorporated into polymeric compositions, the characteristics and/or properties of the polymeric composition, for example, color stability, e.g. as measured by yellowing index, gel content, melt flow index, and oxygen induction time, may be significantly improved. In addition, unlike solid phosphite compositions, liquid phosphite compositions beneficially may be incorporated into polymeric compositions without melting.

In terms of improving color, the stabilizers of the present invention provide improved resistance to discoloration from gas fading, as set forth by AATCC 23 at a temperature of 60° C. Oxides of nitrogen (NOx) in the atmosphere, caused by pollutants, can react with the stabilizers, especially phenolic stabilizers, to trigger discoloration which increases as the exposure time increase. The yellowness index, measured by ASTM D1925, of the polymer stabilized with the stabilizers of the present invention demonstrates a value at 7 days of exposure to NOx of less than 0, e.g., less than –0.5 or less than –0.9; at 18 days of less than 0.7, e.g., less than 0.1 or less than –0.3; at 25 days of less than 1.2, e.g., less than 1.1 or less than 1; at 33 days of less than 1.8, e.g., less than 1.7 or less than 1.65; and at 41 days of less than 3, e.g., less than 2.5 or less than 2.4. This is a significant improvement over resins stabilized with conventional stabilizers.

Gel content may be measured by counting the number of 200 to 400 μm gel sized formations in a square meter of polymeric film. The polymers stabilized with stabilizers of the present invention preferably have a gel content of 200 to 400 μm gel sized formations ranging from 0.01 to 0.5 gel per square meter (gel/m$^2$) of film, e.g., from 0.05 to 0.45 gel/m$^2$, or from 0.1 to 0.42 gel/m$^2$. These gel contents obtained with the stabilizing compositions of the invention are significantly lower than those achieved using conventional stabilizers which typically have gel contents of greater than 1 gel/m$^2$, e.g., greater than 2 gel/m$^2$, or greater than 3 gel/m$^2$. In one embodiment, the polymers stabilized with the stabilizing compositions of the invention have no detectable gel size formations greater than 400 μm. Conventional stabilizers which typically have detectable amount of gel contents greater than 400 μm of less than 5 gel/m$^2$, e.g., less than 2 gel/m$^2$ or less than 0.5 gel/m$^2$.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner.

EXAMPLES

The present invention will be further understood in view of the following non-limiting examples.

Example 1

LLDPE, which is an ethylene-hexene copolymer having a density of 0.918 g/cc and melt flow index of 0.6 to 1.0 g per 10 mins, was stabilized with a 2150 wppm of 1,3,5-tris(4-t-butyl-3-hydroxy-2,6-dimethylbenzyl)-1,3,5-Triazine-2,4,6-(1H,3H,5H)-trione (Lowinox 1790) and tris(nonyl-phenyl)

phosphite (Weston TNPP). The LLDPE was produced in a gas phase polymerization process using metallocene catalyst.

Comparative Example A

LLDPE from Example 1 was stabilized with 2500 wppm of octadecyl-3-(3',5'-di-tert-butyl-4'-hydroxyphenyl)propionate (Anox PP18) and tris(nonyl-phenyl)phosphite (Weston TNPP).

Comparative Example B

LLDPE from Example 1 was stabilized with 2000 wppm of octadecyl-3-(3',5'-di-tert-butyl-4'-hydroxyphenyl)propionate (Anox PP18) and tris(2,4-di-tert-butylphenyl)phosphite (Alkanox 240).

Example 2

Surprisingly and unexpectedly, the gel content measurements of Example 1 and Comparative Examples A and B demonstrated that Example 1 has a significantly lower gel content compared with Comparative Examples A and B as summarized in Table 4 below. Example 1 and Comparative Examples A and B did not contain any anti-gel agents.

TABLE 4

| Example | Gel Counts of 200 to 400 μm (gel/m$^2$) | Gel Counts of 400 μm or greater (gel/m$^2$) |
|---|---|---|
| 1 | Less than 0.42 | 0 |
| A | 2.8-2.9 | Less than 0.5 |
| B | 3.6-3.7 | Less than 0.5 |

Example 3

A gas fading analysis of Example 1 and Comparative Examples A and B demonstrated that Example 1 had low gas fading (AATCC 23) to NOx over the test period as summarized in Table 5 below. The yellow index (YI) is determined by ASTM D1925.

TABLE 5

| NOx Exposure (Days) | Yellow Index (YI) | | |
|---|---|---|---|
| | Example 1 | Comparative A | Comparative B |
| 0 | −1.099 | −1.094 | −0.896 |
| 7 | −0.307 | −0.662 | 0.259 |
| 18 | 0.649 | 0.732 | 2.494 |
| 25 | 1.098 | 1.686 | 3.692 |
| 33 | 1.614 | 2.566 | 4.6 |
| 41 | 2.496 | 4.184 | 6.071 |

What is claimed is:

1. A polyolefin film, comprising:
    a) a polyolefin selected from the group consisting of polyethylene homopolymers, polyethylene copolymers, polypropylene homopolymers, and polypropylene copolymers; and
    b) an effective amount of a stabilizing composition, comprising:
    (1) a sterically hindered phenol of formula I or II:

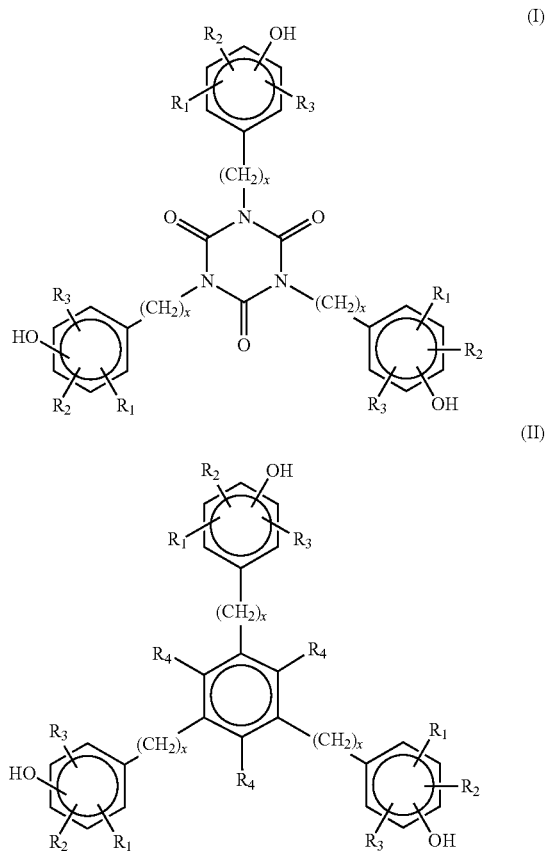

wherein: x is independently 0, 1, 2, or 3; $R_1$, $R_2$, and $R_3$ is independently hydrogen, and $C_1$-$C_{12}$ alkyl, and $C_5$-$C_{10}$ cycloalkyl, provided that at least one of $R_1$, $R_2$, and $R_3$ is not hydrogen; and $R_4$ is independently $C_1$-$C_6$ alkyl; and
    (2) a phosphite selected from the group consisting of triphenyl phosphite, tris(nonyl-phenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,4-dicumylphenyl)pentaerythritol diphosphite, tristearyl sorbitol triphosphite, tris(dipropyleneglycol)phosphite, tetrakis(2,4-di-tert-butylphenyl)-4,4'-biphenylene diphosphonite, and mixtures thereof;
wherein the article has a gel content of 200 to 400 μm gel sized formations of from 0.01 to 0.5 gel per square meter (gel/m$^2$) of the article.

2. The film of claim 1, wherein the film has no detectable gel sized formations that are greater than 400 μm.

3. The film of claim 1, wherein the film has a yellowness index after exposure to NOx for 7 days of less than 0, for 18 days of less than 0.7, for 25 days of less than 1.1, for 33 days of less than 1.7 or for 41 days of less than 2.5.

4. The film of claim 1, wherein the article comprises the stabilizing composition in an amount from 250 to 5000 wppm.

5. The film claim 1, wherein the sterically hindered phenol is of formula I.

6. The film claim 1, wherein the sterically hindered phenol is of formula II.

7. The film of claim 1, wherein the sterically hindered phenol is selected from the group consisting of 1,3,5-tris-(4-tert-butyl-3-hydroxy-2,6-dimethylbenzyl)isocyanurate, 1,3,5-tris-(3,5-dicyclohexyl-4-hydroxybenzyl)isocyanurate, 1,3,5-tris-(3,5-di-tert-butyl-4-hydroxybenzyl)isocyanurate, 1,3,5-tris(4-t-butyl-3-hydroxy-2,6-dimethylbenzyl)-1,3,5-Triazine-2,4,6-(1H,3H,5H)-trione, and 1,3,5-tris-(3,5-di-tert-butyl-4-hydroxybenzyl)-2,4,6-trimethylbenzene.

8. The film of claim 7, wherein the sterically hindered phenol is selected from the group consisting of 1,3,5-tris-(4-tert-butyl-3-hydroxy-2,6-dimethylbenzyl)isocyanurate, 1,3,5-tris-(3,5-dicyclohexyl-4-hydroxybenzyl)isocyanurate, and 1,3,5-tris(4-t-butyl-3-hydroxy-2,6-dimethylbenzyl)-1,3,5-triazine-2,4,6-(1H,3H,5H)-trione.

9. The film of claim 1, wherein the composition is substantially free of anti-gel agents.

10. The film of claim 1, wherein the weight ratio of the sterically hindered phenol to the phosphite composition is from 1:1 to 1:20.

11. The film of claim 1, wherein the polyolefin is produced by free-radical polymerization, Ziegler-Natta catalysts, Phillips-type catalysts, single-site catalysts, and metallocene catalysts.

12. The film of claim 1, wherein the polyolefin is linear low density polyethylene produced from a metallocene catalyst.

13. A polyolefin film, comprising:
    a) a polyolefin selected from the group consisting of polyethylene homopolymers, polyethylene copolymers, polypropylene homopolymers, and polypropylene copolymers: and
    b) an effective amount of a stabilizing composition, comprising:
        (1) a sterically hindered phenol selected from the group consisting of 1,3,5-tris-(4-tert-butyl-3-hydroxy-2,6-dimethylbenzyl)isocyanurate, 1,3,5-tris-(3,5-dicyclohexyl-4-hydroxybenzyl)isocyanurate, and 1,3,5-tris(4-t-butyl-3-hydroxy-2,6-dimethylbenzyl)-1,3,5-triazine-2,4,6-(1H,3H,5H)-trione; and
        (2) a liquid tris(mono-alkyl)phenyl phosphite ester or a liquid mixture of liquid tris(mono-alkyl)phenyl phosphite esters;
    wherein the article has a gel content of 200 to 400 μm gel sized formations of from 0.01 to 0.5 gel per square meter (gel/m$^2$) of the article.

14. The film of claim 13, wherein b) comprises a mixture of two phosphites selected from tris(3-t-butylphenyl)phosphite, tris(2-sec-butylphenyl)phosphite, and tris(4-sec-butylphenyl)phosphite, or a mixture of a phosphite selected from tris(3-t-butylphenyl)phosphite, tris(2-sec-butylphenyl)phosphite, and tris(4-sec-butylphenyl)phosphite with a phosphite selected from tris(2-t-butylphenyl)phosphite, tris(4-t-butylphenyl)phosphite, or tris(2,4-di-t-butylphenyl)phosphite.

15. The film of claim 13, wherein the film has no detectable gel sized formations that are greater than 400 μm.

16. The film of claim 13, wherein the article comprises the stabilizing composition in an amount from 250 to 5000 wppm.

17. The film of claim 13, wherein the composition is substantially free of anti-gel agents.

18. The film of claim 13, wherein the weight ratio of the sterically hindered phenol to the phosphite composition is from 1:1 to 1:20.

19. The film of claim 13, wherein the polyolefin is produced by free-radical polymerization, Ziegler-Nitta catalysts, Phillips-type catalysts, single-site catalysts, and metallocene catalysts.

20. The composition of claim 13, wherein the polyolefin is linear low density polyethylene produced from a metallocene catalyst.

* * * * *